(12) United States Patent
Jones et al.

(10) Patent No.: US 7,125,909 B2
(45) Date of Patent: *Oct. 24, 2006

(54) STERILE PARENTERAL NUTRITION COMPOSITIONS

(75) Inventors: Christopher Buchan Jones, Prestbury (GB); John Henry Platt, Congleton (GB)

(73) Assignee: AstraZeneca UK Limited, London (GB)

( * ) Notice: Subject to any disclaimer, the term of this patent is extended or adjusted under 35 U.S.C. 154(b) by 73 days.

This patent is subject to a terminal disclaimer.

(21) Appl. No.: 10/143,808

(22) Filed: May 14, 2002

(65) Prior Publication Data

US 2003/0134908 A1    Jul. 17, 2003

(51) Int. Cl.
A61K 31/205    (2006.01)

(52) U.S. Cl. .................. 514/556; 514/561; 514/731

(58) Field of Classification Search ................ 514/731, 514/556, 561
See application file for complete search history.

(56) References Cited

U.S. PATENT DOCUMENTS

| | | | |
|---|---|---|---|
| 3,384,545 A | | 5/1968 | Aiello et al. |
| 4,056,635 A | | 11/1977 | Glen et al. |
| 4,073,943 A | | 2/1978 | Wretlind et al. |
| 4,168,308 A | | 9/1979 | Wretlind et al. |
| 4,328,213 A | | 5/1982 | Ecker et al. |
| 4,447,657 A | | 5/1984 | Firth et al. |
| 4,452,817 A | | 6/1984 | Glen et al. |
| 4,567,161 A | | 1/1986 | Posanski et al. |
| RE32,393 E | | 4/1987 | Wretlind et al. |
| 4,798,846 A | * | 1/1989 | Glen et al. .................. 514/731 |
| 5,079,003 A | | 1/1992 | Scaffidi |
| 5,110,809 A | | 5/1992 | Wang et al. |
| 5,714,520 A | * | 2/1998 | Jones et al. .................. 514/731 |
| 5,731,355 A | * | 3/1998 | Jones et al. .................. 514/731 |
| 5,908,869 A | * | 6/1999 | Jones et al. .................. 514/731 |

FOREIGN PATENT DOCUMENTS

| | | |
|---|---|---|
| EP | 0220152 | 4/1987 |
| EP | 0316834 A1 | 5/1989 |
| EP | 0372331 | 6/1990 |
| EP | 0473159 A1 | 3/1992 |
| EP | 0572190 | 12/1993 |
| FR | 2 265 357 | 10/1975 |
| GB | 1472793 | 5/1977 |
| JP | 4-281835 | 7/1992 |
| WO | 90/06055 | 6/1990 |
| WO | 96/29064 | 9/1996 |
| ZA | 93/0069 | 6/1993 |

OTHER PUBLICATIONS

U.S. Data Sheet for Edetate Disodium.
Martindale's Pharmacopeia, 1993, p. 681.
Shiraishi (Abstract) JPA 1283206, Nov. 1989.
Professional Information Brochure, DIPRIVAN (propofol) Injection, Emulsion For IV Administration, Rev L Oct. 1994.
Risuburan (Abstract), JPA 60048916, Mar. 1985.
Derwent Publication Abstract JP2096515, Apr. 1990.
Chemical Abstract No. 113-84881, Morita et al., Ophthamic Solutions Containing Benzalkonium Chloride, P-hydroxybenzoate Esters and Chelating Agents, Sep. 3, 1990.
Trissel, Handbook on Injectable Drugs, 1994, 8th Edition, pp. 63, 115, 125-127, 133, 269, 308, 314-316, 318-319, 484-485, 536-537, 590-591, 612-613, 664-665, 722-723, 770-771, 815, 901-903, 920-921, 934-935, 1007, 1104.
Nakamura et al., Direct Vasoconstrictor and Vasodilator Effects of Propoflin in Isolated Dog Arteries, British Journal of Anaesthesia, Feb. 1992, pp. 193-197.
S. Mouten Perry et al., Effect of I.V. Anaesthesia with Propofol on Drug Distribution and Metabolism in the Dog, British Journal of Anaesthesia, Jan. 1991, pp. 66-72.
Patel et al., Disodium Salt of Edta as an Antimicrobial Agent, Indian Journal of Pharmacy, May 1965, pp. 147-148.
Russell, Effect of Magnesium Ions and Ethylenediamine Tetra-acetic Acid on the Activity of Vancomycin against *Escherichia coli* and *Staphylococcus aureus*, 1967, J. appl. Bact., 30, 395-401.
Russell et al., Ethylenediaminetetra-acetic acid, Inhibition and Destruction of the Microbial Cell, 1971, pp. 209-224.
Chew et al., In Vitro Growth Inhibition of Mastitis Causing Bacteria by Phenolics and Metal Chelators, Journal of Dairy Science, 1985, 68, pp. 3037-3046.
Morita et al., The Effects of Copper and EDTA on the Autoxidation of Phospholipid Emulsions, Agr. Biol. Chem., 1972, vol. 36, No. 7, pp. 1163-1167.
Hart et al., Chelating Agents as Preservative Potentiators, Cosmetic and Drug Preservation: Principles and Practice, Chapter 18, 1985, pp. 323-337.
Postsurgical Infections Associated with an Extrinsically Contaminated Intravenous Anesthetic Agent—California, Illinois, Maine, and Michigan, 19901, Morbidity and Mortality Weekly Report (MMR), Jun. 29, 1990, pp. 426-427, 433.
Bennett et al., Postoperative Infections Traced to Contamination of an Intravenous Anesthetic, Propofol, The New England Journal of Medicine, Jul. 1995, pp. 147-154.
Simmons, CDC Guidelines for the Prevention and Control of Nosocomial Infections; Guidelines for prevention of intravascular infection, American Journal of Infection Control, Oct. 1983, pp. 183-193.

(Continued)

Primary Examiner—Dwayne Jones
(74) Attorney, Agent, or Firm—Morgan, Lewis & Bockius LLP

(57) ABSTRACT

Pharmaceutical compositions containing 2,6-diisopropylphenol (propofol) are described for use as anaesthetics.

A method for their preparation is described, as their use in producing anaesthesia including induction and maintenance of general anaesthesia and sedation.

13 Claims, No Drawings

OTHER PUBLICATIONS

Crocker et al., Microbial Growth Comparisons of Five Commercial Parenteral Lipid Emulsions, Journal of Parenteral and Enteral Nutrition, 1984, pp. 391-395.

D'Angio et al., The Growth of Microorganisms in Total Parenteral Nutrition Admixtures, Journal of Parenteral and Enternal Nutrition, 1987, pp. 394-397.

Melly et al., Microbial Growth in Lipid Emulsions Used in Parenteral Nutrition, Arch Surg, 1975, pp. 1479-1481.

Gilbert et al., Microbial Growth Patterns in a Total Parenteral Nutrition Formulation Containing Lipid Emulsion, Journal of Parenteral and Enteral Nutrition, 1986, pp. 494-497.

Thompson et al., Infection Control of Parenteral Nutrition Solutions, Nutrition in Clinical Practice, Apr. 1991, pp. 49-54.

Grier et al., So Much Writing, So Little Science: A Review of 37 Years of Literature on Edetate Sodium Chelation Therapy, The Annals of Pharmacotherapy, Dec. 1993, pp. 1504-1509.

Haque and Russell, Effect of Ethylenediaminetetraacetic Acid and Related Chelating Agents on Whole Cells of Gram-Negative Bacteria, Antimicrobial Agents and Chemotherapy, May 1974, pp. 447-452.

Haque and Russell, Effect of Chelating Agents on the Susceptiblity of Some Strains of Gram-Negative Bacteria to Some Antibacterial Agents, Antimicrobial Agents and Chemotherapy, Aug. 1974, pp. 200-206.

Russell, Modification of the Bacterial Cell Envelope and Enhancement of Antibiotic Susceptibility, Chapter of the Control of Antibiotic-Resistant Bacteria, Academic Press, 1982, pp. 119-165.

Hart, EDTA-Type Chelating Agents in Personal Care Products, Cosmetics & Toiletries, Apr. 1983, pp. 54-58.

Hart, Chelating agents in cosmetic and toiletry products, Cosmetics & Toiletries, Dec. 1978, pp. 28-30.

Hart, EDTA-Type Chelating Agents in Everyday Consumer Products: Some Medicinal and Personal Care Products, Journal of Chemical Education, Dec. 1984, pp. 1060-1061.

Kabara, GRAS antimicrobial agents for cosmetic products, J. Soc. Cosmet. Chem., Jan./Feb. 1980, pp. 1-10.

Kraniak et al., Effect of Ethylenediaminetetraacetic Acid (EDTA) and Metal ions on Growth of *Staphylococcus aureus* 196E in Culture Media, Journal of Food Science, 1988, pp. 910-913.

Bhagat et al., Growth response of *Pseudomonas stutzeri* RS34 to ethylenediaminetetraacetic acid (EDTA) and its interaction with zinc, Indian Journal of.

Houben et al., Controlling Growth of *Streptococcus faecium* in a Ham Model with Heat and Ethylenediamine Tetraacetic Acid, Tertiary butylhydroquinone or Nisin, Meat Science, 1985, pp. 205-215.

Trissel, Handbook of Injectable Drugs, 1994, pp. 381-383.

Parenteral Preparations, British Pharmacopoeia 1993, vol. II, pp. 746-747.

The Pharmaceutical CODEX, Principles and Practice of Pharmaceutics, Twelfth Edition, pp. 102-103.

The United States Pharmacopeia, The National Formulary, 1995, pp. 1650-1652; 1733-1735; 1681.

Trissel, Handbook of Injectable Drugs, 1994, pp. 464-465, 558-559, 593-599 and 662-663.

Shooter et al., Mineral Requirements for Growth of *Staphylococcus Pyrogenes*, Effect of Magnesium and Calcium Ions, The British Journal of Experimental Pathology, 1955, pp. 341-350.

Sack et al., Factors Affecting The Production of *Staphylocoagulase* in a Chemically Defined Medium, The Ohio Journal of Science, Sep. 1963, pp. 232-240.

Handbook of Pharmaceutical Excipients (cd Wade & Weller), 1994, pp. 176-179.

Martindale The Extra Pharmacopoeia, 29th Edition, The Pharmaceutical Press, London, 1989, pp. 1124-1125.

The Merck Index, 9th Edition, Merch & Co., Inc., Rahway, NJ, USA, 1976 citation 8362 (sodium edetate) & pp. 711, 712, 1115, 581, 394, 309, 310, 590, 805, 857, 261, 385, 463.

Basic & Clinical Pharmacaology, Ed. B.G. Katzung, 4th Edition, 1989, Prentice-Hall International Inc., p. 312.

Organic Chemistry, R.J. Fessenden & J.S. Fessenden, 2nd Edition, 1982, Willard Grant Press, pp. 888.

Guide to Microbial Control in Pharmaceuticals, Ed. S. Denyer & R. Baird, published 1990, p. 257.

MIMA Australia, Crow's Nest, NSW, Australia, pp. 16-693 to 16-694.

R.Voigt, Pharmazeutische Technologie fur Studium und Beruf, 7th Edition—Berlin, 1993 (Ullstein Mosby), chapter 20.5.3.3.1 (pp. 474-476) and chapter 26.4.3.3.4 (p. 591).

Whalley, G., Preservative Properties of EDTA, Manufacturing-Chemist, 1991, vol. 62, No. 9, pp. 22-23.

* cited by examiner

STERILE PARENTERAL NUTRITION COMPOSITIONS

The present invention relates to 2,6-diisopropylphenol, known as propofol, and in particular to new pharmaceutical compositions containing propofol.

Propofol is an injectable anaesthetic which has hypnotic properties and can be used to induce and maintain general anaesthesia and for sedation for example in Intensive Care Units. Propofol is a highly successful anaesthetic and is marketed under the trademark 'Diprivan' for use in treating humans and under the trademark 'Rapinovet' for veterinary use.

Injectable anaesthetics, such as propofol, are administered directly into the blood stream. This gives rise to a rapid onset of anaesthesia influenced almost entirely by the rate at which the anaesthetic agent crosses the blood-brain barrier. It is therefore necessary for the anaesthetic agent to have sufficient lipid solubility to be able to cross this barrier and depress the relevant mechanisms of the brain. However highly lipid soluble molecules are generally poorly soluble in water and thus are difficult to formulate for intravenous injection. In some cases it may be possible to obtain a water soluble salt of the anaesthetic agent which releases a lipid soluble free base in vivo. This is not possible in many cases and, despite considerable research, it did not prove to be feasible with propofol. Thus it was necessary to conduct very substantial research and development into the formulation of propofol in order to obtain pharmaceutical compositions for administration to warm-blooded animals including humans.

The present applicants identified the anaesthetic properties of propofol and filed UK patent application no 13739/74 which was granted as United Kingdom Patent 1472793. Corresponding patents have been granted in the USA (U.S. Pat. No. 4,056,635, U.S. Pat. No. 4,452,817 and U.S. Pat. No. 4,798,846) and many other territories.

This patent claims inter alia a sterile pharmaceutical composition which comprises propofol in association with a sterile pharmaceutically-acceptable diluent or carrier the composition being suitable either directly or after dilution with a liquid diluent for parenteral administration to a warm-blooded animal.

In one aspect, UK 1472793 described the composition as preferably aqueous with propofol in sterile admixture with water and a surfactant or other solubilising agent. In another aspect the composition was described as aqueous with propofol in sterile admixture with water and an additional water-miscible, non-aqueous solvent. In a further aspect the composition was described as an oil-in-water emulsion in which propofol, either alone or dissolved in a water-immiscible solvent, is emulsified with water by means of a surfactant. In yet a further aspect the composition was described as a sterile solid or semi-solid mixture of propofol with a solid diluent, for example lactose, saccharin sodium or a cyclodextran which composition is suitable for dilution with a sterile aqueous diluent.

The patent describes many particular Examples of injectable compositions containing propofol including Examples with various surfactants, various solubilising agents, additional solvents, additional constituents (selected from stabilisers, preservatives and antioxidants), buffering agents and tonicity modifiers.

The present applicants conducted a wide range of studies to determine which type of formulation would be most appropriate for development to provide a formulation for marketing. After considerable effort a formulation of propofol and the surfactant Cremophor EL (Cremophor is a trade mark for a polyoxyethylene castor oil derivative) in water was selected. Cremophor EL was used as the carrier to solubilise the existing intravenous anaesthetic alphaxalone/alphadolone ('Althesin') and a modified form of Cremophor was used as the carrier to solubilise the intravenous anaesthetic propanidid ('Epontol').

The present applicants conducted a detailed series of studies in animals and ultimately administered the formulation to over 1000 humans. However, after about five or six years, anaphylactoid reactions were reported in a very small number of patients. Anaphylactoid reactions are allergic-type reactions. It was not clear that Cremophor EL had caused the anaphylactoid reactions in all instances but the present applicants concluded that an alternative formulation of propofol would have to be found and developed.

A substantial amount of work on alternative formulations was performed and an oil-in-water emulsion was eventually selected for development. This was developed and in 1986 was launched in a number of markets under the trade mark 'Diprivan'. Since then this formulation has been launched in many markets throughout the world and propofol is highly successful being regarded by anaesthetists as a drug of great merit having unique qualities. In summary propofol is a short-acting anaesthetic, suitable for both induction and maintenance of general anaesthesia, for sedation to supplement regional analgesic techniques, for sedation of ventilated patients receiving intensive care and for conscious sedation for surgical and diagnostic procedures in Intensive Care Units. Propofol may be administered by single or repeated intravenous bolus injections or by continuous infusion. It is very rapidly removed from the blood stream and metabolised. Thus the depth of anaesthesia is easily controlled and patient recovery on discontinuing the drug is usually rapid and the patient is often significantly more clear headed as compared to after administration of other anaesthetics. Side-effects such as nausea and vomiting occur significantly less frequently following administration of propofol than following other general anaesthetic techniques such as with inhalational anaesthetics.

The present applicants have considered extending the range of propofol formulations in order to give the anaesthetist a wider armamentarium from which to select an appropriate drug. For example applicants have developed, as an alternative, an oil-in-water emulsion formulation of propofol wherein the concentration of propofol is twice that of the presently marketed drug.

In considering appropriate further formulations it is desirable to maintain the qualities that make 'Diprivan' of such merit, such as those aforementioned and provide a formulation with acceptable chemical and physical stability and which is readily manipulable by the anaesthetist or Intensive Care Unit (ICU) specialist.

An increasing proportion of the usage of 'Diprivan' is in the sedation of seriously ill patients particularly in Intensive Care Units and the like. In the sedation of such seriously ill patients administration of 'Diprivan' is typically by means of infusion. This requires the use of a 'giving set', which involves the linkage of a reservoir (typically a vial or syringe), of propofol, via appropriate tubing, to a luer connector and thence to a needle positioned in the patient's vein.

Microbial contamination of parenteral fluids used in 'giving sets' of this type has been recognised as one of many causes of nosocomial infection amongst ICU patients. Accordingly, for example in the USA, the general requirements of the Federal Food and Drug Administration (FDA) are that such 'giving sets' are changed frequently and in the case of 'Diprivan', it is required that the 'giving sets' are changed at least every 6 or 12 hours dependent on the presentation being used.

Intensive Care environments are busy and, as in other parts of the health services, there are pressures for cost-containment. The changing of 'giving sets' at least every 6 or 12 hours is relatively time-consuming for the highly skilled ICU nurse, Intensive Care Specialist or anaesthetist. This would particularly be the case when a number of seriously ill patients in an ICU are being infused at the same time.

Therefore, the applicants have sought to develop a new formulation of propofol which would enable 'giving sets' to be changed significantly less frequently (for example every 24 hours). This would be much more convenient for the nurse, Intensive Care Specialist or anaesthetist; would lower the pressure on staff, would result in fewer manipulations of 'giving sets' and may contribute to cost-saving in the ICU environment.

We have conducted substantial research and have found that the addition of small amounts of a selected agent to 'Diprivan' will enable the formulation to be administered in 'giving sets' that require changing significantly less frequently is the case; in other words the time for administration and time between changes of the giving sets has been significantly improved. This increase in such times enables packs of increased size to be administered, increasing convenience for the users, decreasing wastage of 'Diprivan' and contributing to cost-containment.

Furthermore, in the unlikely event of mishandling leading to accidental extrinsic contamination, the formulation will minimise the chance of microbial growth.

Our own UK Patent 1472793 discloses that formulations of propofol may optionally contain one or more additional constituents selected from stabilisers, preservatives and antioxidants, for example parabens derivatives, for example propyl p-hydroxybenzoate, butylated hydroxytoluene derivatives, ascorbic acid and sodium metabisulphite; metal ion sequestering agents, for example sodium edetate; and antifoaming agents, for example a silicone derivative, for example dimethicone or simethicone.

There is a difficulty in the addition of known preservatives to oil-in-water emulsions such as 'Diprivan'. As stated above, 'Diprivan' is an anaesthetic used for induction and maintenance of general anaesthesia and for sedation. The volumes administered can be considerable, particularly in the case of sedation. Accordingly, significant volumes of preservative may be administered to the patient receiving treatment. Thus very careful selection of additive must be made in order to satisfy drug Regulatory Authorities; particularly as the use of preservatives in single-dose, terminally sterilised, parenteral injectables is not suggested and/or is the subject of cautionary statements in various Guidelines, for example those of the US, UK and European Pharmacopeias.

Furthermore there is a particular problem in the inclusion of additives in an oil-in-water emulsion for parenteral administration. It is believed that for effectiveness, the antimicrobial properties of any preservative have to be exerted in the aqueous phase. Thus, a preservative with lipophilic properties incorporated at typical usage levels would not be effective as, although there would be some partitioning between the phases, there would be insufficient material in the aqueous phase. Increasing the overall quantity of such preservative would result in unacceptably high levels of preservative in the lipid layer leading to toxicity problems at least.

On the other hand, addition of a preservative with hydrophilic properties, eg an ionic material, also leads to problems. The addition of ionic material to an oil-in-water emulsion tends to destabilise the emulsion. With a higher ionic load (that is concentration of ionic material) the stabilising electrical charge (Zeta potential) on the oily droplets can change. Such electrical charge changes increase the probability of droplet collisions and increase the physical instability of the emulsion.

We studied the possibility of adding one of a number of antimicrobial agents to the oil-in-water emulsion. Such an agent would have to have no significant detrimental effect on the physical and chemical stability of the emulsion. Furthermore, such an agent would have to provide the antimicrobial activity being sought.

A number of potential agents were found to cause instability of the emulsion. Other potential agents failed to provide the level of antimicrobial activity being sought. In addition, we were seeking an agent that would provide these levels of activity at as low a concentration as possible in order to minimise the potential for physical instability and to minimise safety concerns.

After significant effort including consideration of the known preservatives phenylmercuric acetate, phenylmercuric nitrate, benzyl alcohol, chlorobutanol, chlorocresol and phenol and the study of the known preservatives sodium metabisulphite, sodium sulphite, sodium methyl hydroxybenzoate and sodium propyl hydroxybenzoate, we were unable to find a preservative that met our requirements. We then investigated the possible use of other agents which might have the action that we sought. We unexpectedly found that edetate, which is not regarded as a broad spectrum antimicrobial agent was the only agent that would meet our requirements. As referred to above, edetate as the sodium salt is mentioned in our UK Patent 1472793 as a possible metal ion sequestering agent. Sodium edetate is included in two of the many Cremophor-containing examples of that Patent.

Accordingly the present invention provides a sterile pharmaceutical composition for parenteral administration which comprises an oil-in-water emulsion in which propofol dissolved in a water-immiscible solvent, is emulsified with water and stabilised by means of a surfactant, and which further comprises an amount of edetate sufficient to prevent significant growth of microorganisms for at least 24 hours (in the event of adventitious, extrinsic contamination).

By an oil-in-water emulsion we mean a distinct two-phase system that is in equilibrium and in effect, as a whole, is kinetically stable and thermodynamically unstable. This is in complete contrast to a micellar formulation, for example with Cremophor EL, which is thermodynamically stable.

By the term "edetate" we mean ethylenediaminetetraacetic acid (EDTA) and derivatives thereof, for example the disodium derivative is known as disodium edetate. In general suitable edetates of this invention are those salts having lower affinity for EDTA than calcium. Particular derivatives of use in the present invention include trisodium edetate, tetrasodium edetate and disodium calcium edetate. The nature of the edetate is not critical, provided that it fulfils the function of preventing significant growth of microorganisms for at least 24 hours in the event of adventitious extrinsic contamination (e.g. preferably no more than 10-fold increase following a low level of extrinsic contamination, such as $10-10^3$ colony forming units, at temperatures in the range of 20–25° C.). As can be seen from the experimental section, sodium calcium edetate has some advantages over other additives but disodium edetate is exceptional. Accordingly, most preferably the edetate is disodium edetate.

Typically the edetate will be present in the compositions of the present invention in a molar concentration (with respect to the EDTA free acid) in the range $3 \times 10^{-5}$ to $9 \times 10^{-4}$. Preferably the edetate is present in the range $3 \times 10^{-5}$ to $7.5 \times 10^{-4}$, for example in the range $5 \times 10^{-5}$ to $5 \times 10^{-4}$ and more preferably in the range $1.5 \times 10^{-4}$ to $3.0 \times 10^{-4}$, most preferably about $1.5 \times 10^{-4}$.

A composition of the present invention typically comprises from 0.1 to 5%, by weight, of propofol. Preferably the composition comprises from 1 to 2% by weight of propofol and, in particular, about 1% or about 2%.

In another aspect of the invention propofol alone is emulsified with water by means of a surfactant. It is preferred that propofol is dissolved in a water-immiscible solvent prior to emulsification.

The water-immiscible solvent is suitably present in an amount that is up to 30% by weight of the composition, more suitably 5–25%, preferably 10–20% and in particular about 10%.

A wide range of water-immiscible solvents can be used in the compositions of the present invention. Typically the water-immiscible solvent is a vegetable oil, for example soy bean, safflower, cottonseed, corn, sunflower, arachis, castor or olive oil. Preferably the vegetable oil is soy bean oil. Alternatively, the water-immiscible solvent is an ester of a medium or long-chain fatty acid for example a mono-, di-, or triglyceride; or is a chemically modified or manufactured material such as ethyl oleate, isopropyl myristate, isopropyl palmitate, a glycerol ester or polyoxyl hydrogenated castor oil. In a further alternative the water-immiscible solvent may be a marine oil, for example cod liver or another fish-derived oil. Suitable solvents also include fractionated oils for example fractionated coconut oil or modified soy bean oil. Furthermore, the compositions of the present invention may comprise a mixture of two or more of the above water-immiscible solvents.

Propofol, either alone or dissolved in a water-immiscible solvent, is emulsified by means of a surfactant. Suitable surfactants include synthetic non-ionic surfactants, for example ethoxylated ethers and esters and polypropylene-polyethylene block co-polymers, and phosphatides for example naturally occuring phosphatides such as egg and soya phosphatides and modified or artificially manipulated phosphatides (for example prepared by physical fractionation and/or chromatography), or mixtures thereof. Preferred surfactants are egg and soya phosphatides.

The composition of the present invention is suitably formulated to be at physiologically neutral pH, typically in the range 6.0–8.5, if necessary by means of alkali such as sodium hydroxide.

The composition of the present invention may be made isotonic with blood by the incorporation of a suitable tonicity modifier for example glycerol.

The composition of the present inventions are typically sterile aqueous formulations and are prepared according to conventional manufacturing techniques using for example aseptic manufacture or terminal sterilisation by autoclaving.

The compositions of the present invention are useful as anaesthetics which includes sedation and induction and maintenance of general anaesthesia. Accordingly in another aspect the present invention provides a method of producing anaesthesia (including sedation and induction and maintenance of general anaesthesia) in a warm-blooded animal, including humans, which comprises administering parenterally a sterile aqueous pharmaceutical composition which comprises an oil-in-water emulsion in which propofol, either alone or in a water-immiscible solvent, is emulsified with water and stabilised by means of a surfactant and which further comprises an effective amount of edetate.

Dosage levels of propofol for producing general anaesthesia, both induction (for example about 2.0–2.5 mg/kg for an adult) and maintenance (for example about 4–12 mg/kg/hr), and for producing a sedative effect (for example 0.3–4.5 mg/kg/hr), may be derived from the substantial literature on propofol. Furthermore the anaesthetist and/or physician would modify the dose to achieve the desired effect in any particular patient, in accordance with normal skill in the art.

The advantages referred to above for including edetate in propofol compositions apply also to intravenous fat emulsions which typically are administered, to patients in need thereof, over periods of a day or more. Intravenous fat emulsions (also known as parenteral nutrition emulsions) are administered, usually by infusion, to patients having requirements for additional calories and adequate nutrition, by oral or other means, is not desirable or is not possible. Intravenous fat emulsions typically maintain a positive nitrogen balance and provide an adequate source of energy (e.g. as fat), vitamins and trace elements. Such emulsions are used typically in intensive care environments but also in other hospital and domestic settings. Examples of such intravenous fat emulsions include Intralipid (marketed by Pharmacia), Lipofundin (Braun) and Travamulsion (Baxter). Intralipid, Lipofundin and Travamulsion are all trademarks.

Accordingly in another aspect, the present invention provides an intravenous fat emulsion which comprises an amount of edetate sufficient to prevent significant growth of microorganisms for at least 24 hours. In particular the present invention provides a sterile, aqueous composition for parenteral administration which comprises an oil-in-water emulsion in which a water-immiscible solvent is emulsified with water and stabilised by means of a surfactant and which further comprises an amount of edetate sufficient to prevent significant growth of microorganisms for at least 24 hours.

Furthermore, it has been proposed that various drugs may be administered in oil-in-water emulsions, for example see U.S. Pat. No. 4,168,308. Accordingly in a further aspect, the present invention provides a sterile, aqueous composition for parenteral administration which comprises an oil-in-water emulsion containing a therapeutic or pharmaceutical agent, in which the agent, either alone or dissolved in a water-immiscible solvent, is emulsified with water and stabilised by means of a surfactant and which further comprises an amount of edetate sufficient to prevent significant growth of microorganisms for at least 24 hours.

Suitable therapeutic or pharmaceutical agents are those capable of being administered parenterally in an oil-in-water emulsion. Typically such agents are lipophilic compounds and may for example be antifungal agents, anaesthetics, antibacterial agents, anti-cancer agents, anti-emetics, agents acting on the central nervous system such as diazepam, steroids, barbiturates and vitamin preparations. In particular the present invention relates to such oil-in-water emulsions which typically are administered, to patients in need thereof, over periods of a day or more.

Comments herein relating to typical and preferred propofol compositions of this invention and the preparation thereof apply *mutatis mutandis* to intravenous fat emulsions and to oil-in-water emulsions containing a therapeutic or pharmaceutical agent.

EXPERIMENTAL

| Quantities: | % (weight) |
|---|---|
| propofol | 1.0 |
| soy bean oil | 10.0 |
| egg phosphatide | 1.2 |
| glycerol | 2.25 |
| disodium edetate dihydrate | 0.0055 |
| (equivalent to disodium edetate 0.005) | |
| sodium hydroxide | q.s. |
| Water for Injections | to 100 |

Preparation:

All processing stages are carried out under Nitrogen and weights refer to weight in the final volume.

A sterile aqueous oil-in-water emulsion for parenteral administration is prepared as follows:

1. An aqueous phase is prepared from glycerol (2.25% by weight), disodium edetate dihydrate (0.0055% by weight), sodium hydroxide (typically 60mgL$^{-1}$) and Water for Injections. This mixture is stirred and taken to a temperature of approximately 65° C.

2. The aqueous phase is passed through a filter to remove particulate matter and transferred to a mixing vessel.

3. In parallel to the above, an oil phase is prepared from soy bean oil (10.0% by weight), propofol (1.0% by weight) and egg phosphatide (1.2% by weight) in a vessel. The mixture is stirred at a temperature of approximately 75° C. until all ingredients are dissolved.

4. The mixture is passed through a filter to remove particulate matter and added to the aqueous phase via a static mixer.

5. The contents of the mixing vessel are stirred and maintained at a temperature of approximately 65° C. This mixture is then circulated through a high pressure homogeniser and cooler (heat exchange system) until the required globule size [mean globule size of approximately 250 nanometres] is achieved.

6. The resultant oil-in-water emulsion is cooled and transferred into a filling vessel.

7. The emulsion is then filtered and filled into containers under nitrogen and autoclaved.

The final filtered emulsion may be filled into containers of various volumes for example ampoules (20 ml), vials (50 ml and 100 ml) and pre-filled syringes.

Diagram:

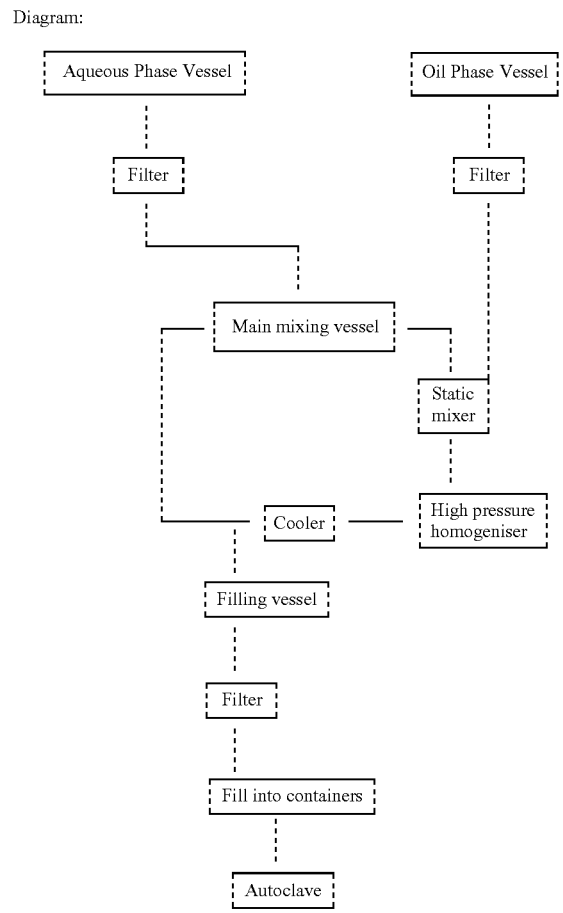

An oil-in-water emulsion containing 2% (by weight) of propofol may be prepared in a similar manner using the following quantities of ingredients:

| Quantities: | % (weight) |
|---|---|
| propofol | 2.0 |
| soy bean oil | 10.0 |
| egg phosphatide | 1.2 |
| glycerol | 2.25 |
| disodium edetate dihydrate | 0.0055 |
| sodium hydroxide | q.s. |
| Water for Injections | to 100 |

Further oil-in-water emulsions containing 1% (by weight) of propofol may be prepared in a similar manner using the following quantities of ingredients:

| Quantities: | % (weight) | % (weight) |
|---|---|---|
| propofol | 1.0 | 1.0 |
| soy bean oil | 5.0 | — |
| fractionated coconut oil (Miglyol 812N) | 5.0 | 10.0 |
| egg phosphatide | 1.2 | 1.2 |
| glycerol | 2.25 | 2.25 |
| disodium edetate dihydrate | 0.0055 | 0.0055 |
| sodium hydroxide | q.s. | q.s. |
| Water for Injections | to 100 | to 100 |

* Miglyol is a trade mark

Biological Activity

The formulations are administered parenterally to groups of 10 male mice (18–22 g) at a dose of 5–40 mg/kg. Sedation and anaesthesia are observed dependent on dose.

Microbiological Activity (Comparative)

Formulations containing various additives were prepared by adding a concentrated aqueous solution of the additive to the commercially available oil-in-water formulation of propofol (1%) (Diprivan : Trade Mark of Zeneca Ltd). The pH of these formulations was approximately 7.5.

Broth cultures of four standard USP (United States Pharmacopeia) preservative efficacy test organisms were added to these test formulations at approximately 200 colony forming units per ml. The test formulations were incubated at 30° C. and tested for viable counts after 24 and 48 hours.

Results

Formulation With Sodium Metabisulphite (0.1%)

| Test Organism | $LOG_{10}$ SURVIVORS PER ML | | |
|---|---|---|---|
| | Zero | 24 hours | 48 hours |
| S. aureus | 2.4 | 4.1 | 4.7 |
| E. coli | 2.2 | 8.9 | 8.7 |
| C. albicans | 2.8 | 4.4 | 7.9 |
| Ps. aeruginosa | 2.8 | 4.8 | 8.9 |

Discolouration of the formulation occurred showing chemical instability.

Formulation With Sodium Sulphite (0.1%)

| Test Organism | $LOG_{10}$ SURVIVORS PER ML | | |
|---|---|---|---|
| | Zero | 24 hours | 48 hours |
| S. aureus | 2.8 | 5.7 | 6.2 |
| E. coli | 1.6 | 7.8 | 8.9 |
| C. albicans | 2.9 | 4.1 | 5.8 |
| Ps. aeruginosa | 2.2 | 6.7 | 6.9 |

Formulation With Hydroxybenzoates (0.2% Methyl/0.02% Propyl)

| Test Organism | $LOG_{10}$ SURVIVORS PER ML | | |
|---|---|---|---|
| | Zero | 24 hours | 48 hours |
| S. aureus | 2.9 | 6.6 | 6.7 |
| E. coli | 1.9 | 4.7 | 7.4 |
| C. albicans | 2.8 | 3.0 | 3.2 |
| Ps. aeruginosa | 2.4 | 2.2 | 5.8 |

Formulation With Sodium Calcium Edetate (0.1%)

| Test Organism | $LOG_{10}$ SURVIVORS PER ML | | |
|---|---|---|---|
| | Zero | 24 hours | 48 hours |
| S. aureus | 2.2 | 3.3 | 6.9 |
| E. coli | 2.6 | <1.3 | <1.3 |
| C. albicans | 2.9 | 3.1 | 3.8 |
| Ps. aeruginosa | 2.8 | 6.8 | 8.2 |

Formulation With Disodium Edetate Dihydrate (0.1%)

[pH Approximately 5.5]

| Test Organism | $LOG_{10}$ SURVIVORS PER ML | | |
|---|---|---|---|
| | Zero | 24 hours | 48 hours |
| S. aureus | 0.7 | 0.3 | <1.0 |
| E. coli | 1.2 | 0.3 | <1.0 |
| C. albicans | 1.0 | 0.8 | <1.0 |
| Ps. aeruginosa | 1.3 | <1.0 | <1.0 |

Microbiological Activity (Further Comparative Results)

Washed suspensions of four standard USP (United States Pharmacopeia) preservative efficacy test organisms were added to these test formulations at approximately 100 colony forming units per ml. The test formulations were incubated at 25° C. and tested for viable counts after 24 and 48 hours in duplicate; both results are reported.

'Diprivan' (1% Propofol)

| Test Organism | $LOG_{10}$ SURVIVORS PER ML | | |
|---|---|---|---|
| | Zero | 24 hours | 48 hours |
| S. aureus | 2.0 | 4.3 | 5.7 |
| | 2.0 | 4.6 | 5.7 |
| E. coli | 1.7 | 8.1 | 7.9 |
| | 1.6 | 7.8 | 8.1 |
| C. albicans | 1.5 | 2.8 | 2.6 |
| | 1.5 | 2.8 | 3.6 |
| Ps. aeruginosa | 1.5 | 4.9 | 8.4 |
| | 1.5 | 3.9 | 8.0 |

Formulation With Disodium Edetate Dihydrate (0.0055%)

| Test Organism | $LOG_{10}$ SURVIVORS PER ML | | |
|---|---|---|---|
| | Zero | 24 hours | 48 hours |
| S. aureus | 2.0 | 1.3 | 0.5 |
| | 2.0 | 1.1 | 1.0 |
| E. coli | 1.6 | 1.1 | ND |
| | 1.4 | 1.1 | ND |
| C. albicans | 1.6 | 1.6 | 2.0 |
| | 1.5 | 1.3 | 2.1 |
| Ps. aeruginosa | 1.6 | 1.0 | 0.8 |
| | 1.5 | ND | 0.7 |

The above formulation has been further assessed against other relevant organisms.

In a similar manner, microbiological data have been obtained for the corresponding formulation containing 2% propofol.

Intravenous Fat Emulsion

[Comprising Soy Bean Oil (10%), Egg Phosphatide (1.2%), Glycerol (2.25%), Sodium Hydroxide (qs) and Water for Injections]

| Test Organism | $LOG_{10}$ SURVIVORS PER ML | | |
|---|---|---|---|
| | Zero | 24 hours | 48 hours |
| S. aureus | 2.0 | 6.5 | 6.6 |
| | 2.0 | 6.6 | 6.7 |
| E. coli | 1.5 | 8.0 | 8.3 |
| | 1.6 | 7.9 | 8.1 |
| C. albicans | 1.5 | 1.2 | 6.0 |
| | 1.4 | 3.5 | 5.6 |
| Ps. aeruginosa | 1.3 | 6.6 | 8.1 |
| | 1.5 | 6.9 | 8.1 |

Intravenous Fat Emulsion (as above) With Disodium Edetate Dihydrate (0.0055%)

| Test Organism | $LOG_{10}$ SURVIVORS PER ML | | |
|---|---|---|---|
| | Zero | 24 hours | 48 hours |
| S. aureus | 2.0 | 1.4 | ND |
| | 2.0 | 1.4 | ND |
| E. coli | 1.6 | ND | ND |
| | 1.5 | ND | ND |
| C. albicans | 1.5 | 1.8 | 2.4 |
| | 1.5 | 2.1 | 2.2 |
| Ps. aeruginosa | 1.6 | ND | ND |
| | 1.5 | ND | ND |

ND: No organisms detected on the 1 ml pour plates

The above formulation has been further assessed against other relevant organisms.

The test organisms identified above are *Staphylococcus aureus* ATCC 6538, *Escherichia coli* ATCC 8739, *Pseudomonas aeruginosa* ATCC 9027 and *Candida albicans* ATCC 10231.

In a preferred embodiment the present invention provides a sterile pharmaceutical composition which comprises an oil-in-water emulsion in which propofol, dissolved in a water-immiscible solvent, is emulsified with water and stabilised by means of a surfactant, and which further comprises an amount of edetate sufficient to prevent a no more than 10-fold increase in growth of each of *Staphylococcus aureus* ATCC 6538, *Escherichia coli* ATCC 8739, *Pseudomonas aeruginosa* ATCC 9027 and *Candida albicans* ATCC 10231 for at least 24 hours as measured by a test wherein a washed suspension of each said organism is added to a separate aliquot of said composition at approximately 50 colony forming units per ml, at a temperature in the range 20–25° C., said aliquots are incubated at 20–25° C. and are tested for viable counts after 24 hours.

What is claimed is:

1. A sterile parenteral nutrition composition comprising an oil-in-water emulsion in which a water-immiscible nutritional agent is emulsified with water and stabilised by means of a surfactant, and which further comprises an amount of edetate in a molar concentration in the range of from $3\times10^{-5}$ to $9\times10^{-4}$.

2. The sterile parenteral nutrition composition according to claim 1, wherein the molar concentration of edetate in said composition is within the range of from $3\times10^{-5}$ to $7.5\times10^{-4}$.

3. The sterile parenteral nutrition composition according to claim 2, wherein the molar concentration of edetate in said composition is within the range of from $1.5\times10^{-4}$ to $3.0\times10^{-4}$.

4. The sterile parenteral nutrition composition according to claim 3, wherein the molar concentration of edetate in said composition is about $1.5\times10^{-4}$.

5. The sterile parenteral nutrition composition according to claim 1, wherein the water-immiscible nutritional agent is a vegetable oil.

6. The sterile parenteral nutrition composition according to claim 5, wherein the vegetable oil is soy bean oil.

7. The sterile parenteral nutrition composition according to claim 1, wherein the surfactant is a naturally occurring phosphatide.

8. The sterile parenteral nutrition composition according to claim 7, wherein the phosphatide is egg phosphatide or soya phosphatide.

9. The sterile parenteral nutrition composition according to claim 1, wherein the pH of said composition is between about 6.0 and about 8.5.

10. The sterile parenteral nutrition composition according to claim 9, wherein said composition additionally comprises sodium hydroxide.

11. The sterile parenteral nutrition composition according to claim 1, wherein said composition is isotonic with blood.

12. The sterile parenteral nutrition composition according to claim 11, wherein said composition is made isotonic with blood by incorporation of glycerol.

13. The sterile parenteral nutrition composition according to claim 1, wherein the edetate is disodium edetate.

* * * * *